(12) United States Patent
Masson et al.

(10) Patent No.: US 9,750,451 B2
(45) Date of Patent: Sep. 5, 2017

(54) ACTIVE ACOUSTIC PRESSURE MAPPING SYSTEM

(71) Applicant: Socpra Sciences Et Genie S.E.C., Sherbrooke (CA)

(72) Inventors: Patrice Masson, Sherbrooke (CA); Nicolas Quaegebeur, Sherbrooke (CA); Pierre-Claude Ostiguy, Sherbrooke (CA); Nicolas Beaudet, Sherbrooke (CA); Philippe Sarret, Sherbrooke (CA)

(73) Assignee: Socpra Sciences Et Genie S.E.C., Sherbrooke (CA)

( * ) Notice: Subject to any disclaimer, the term of this patent is extended or adjusted under 35 U.S.C. 154(b) by 123 days.

(21) Appl. No.: 14/419,257

(22) PCT Filed: Aug. 1, 2013

(86) PCT No.: PCT/CA2013/000688
§ 371 (c)(1),
(2) Date: Feb. 3, 2015

(87) PCT Pub. No.: WO2014/019075
PCT Pub. Date: Feb. 6, 2014

(65) Prior Publication Data
US 2015/0185898 A1    Jul. 2, 2015

Related U.S. Application Data

(60) Provisional application No. 61/679,232, filed on Aug. 3, 2012.

(51) Int. Cl.
*A61B 5/00* (2006.01)
*A61B 5/103* (2006.01)
(Continued)

(52) U.S. Cl.
CPC .......... *A61B 5/4561* (2013.01); *A61B 5/1036* (2013.01); *G06F 3/0436* (2013.01); *G06K 9/00006* (2013.01); *A61B 2560/0223* (2013.01)

(58) Field of Classification Search
None
See application file for complete search history.

(56) References Cited

U.S. PATENT DOCUMENTS 5,283,559 A * 2/1994 Kalendra .............. G06F 3/0418
                                                 345/156
5,456,256 A * 10/1995 Schneider ............ A61B 5/1172
                                                 600/445

(Continued)

FOREIGN PATENT DOCUMENTS

CA    2175691 A1    5/1995
CA    2604969 A1    10/2006
(Continued)

*Primary Examiner* — Kent Chang
*Assistant Examiner* — Nathan Brittingham
(74) *Attorney, Agent, or Firm* — Gowling WLG (Canada); Benoit Yelle (57) ABSTRACT

Method and apparatus for determining that a pressure field is applied on a structure. A plurality of acoustic waves are generated within the structure using at least one wave generator and a plurality of measurements of the acoustic waves is taken using at least one wave sensor. A pressure field applied to a surface of the structure is determined by processing at least two of the plurality of measurements. The wave generator and the wave sensor may be piezoelectric elements, which may alternate between acting as the wave generator and the wave sensor. Processing the measurements may comprise obtaining a differential measurement value and comparing the value to a threshold. Determining that the pressure field is applied may comprise processing the measurements using a model based on acoustic wave propaga- (Continued)

tion or experimental results. The processing may provide a mapping of the pressure field of an object on the structure.

36 Claims, 6 Drawing Sheets

(51) Int. Cl.
*G06F 3/043* (2006.01)
*G06K 9/00* (2006.01)

(56) References Cited

U.S. PATENT DOCUMENTS

| | | | | |
|---|---|---|---|---|
| 6,273,027 | B1 * | 8/2001 | Watson | A01K 15/02 |
| | | | | 119/712 |
| 7,903,090 | B2 * | 3/2011 | Soss | G06F 3/0414 |
| | | | | 345/173 |
| 2005/0012724 | A1 * | 1/2005 | Kent | G06F 3/0418 |
| | | | | 345/177 |
| 2012/0287087 | A1 * | 11/2012 | Lu | G06F 3/0418 |
| | | | | 345/178 |
| 2013/0094126 | A1 * | 4/2013 | Rappoport | G02B 27/01 |
| | | | | 361/679.01 |
| 2013/0234995 | A1 * | 9/2013 | Son | G06F 3/043 |
| | | | | 345/177 |
| 2013/0287272 | A1 * | 10/2013 | Lu | G06F 3/041 |
| | | | | 382/124 |
| 2014/0118307 | A1 * | 5/2014 | Berget | G06F 3/0433 |
| | | | | 345/177 |

FOREIGN PATENT DOCUMENTS

| | | |
|---|---|---|
| CA | 2611681 A1 | 3/2007 |
| WO | WO9807127 A1 | 2/1998 |

\* cited by examiner

Figure 8

ACTIVE ACOUSTIC PRESSURE MAPPING SYSTEM

CROSS REFERENCE TO RELATED APPLICATIONS

U.S. Provisional Patent Application Ser. No. 61/310,996 filed on Mar. 5, 2010 and entitled "METHOD FOR IMAGING A STRUCTURAL CONDITION OF A STRUCTURE" is hereby incorporated by reference.

PCT Patent Application number PCT/CA2011/000254 filed on Mar. 4, 2011 claiming priority from the U.S. Provisional Patent Application Ser. No. 61/310,996, published under WO/2011/106890 on Sep. 9, 2011 and entitled "METHOD AND APPARATUS FOR PROVIDING A STRUCTURAL CONDITION OF A STRUCTURE" is hereby incorporated by reference.

The priority U.S. Provisional Patent Application Ser. No. 61/679,232 filed on Aug. 3, 2012 and entitled "ACTIVE ACOUSTIC PRESSURE MAPPING SYSTEM" is hereby incorporated by reference.

TECHNICAL FIELD

The present invention relates to a sensitive surface and, more particularly, to a surface that is sensitive to contact pressure and position of an object.

BACKGROUND

Touch screens that are most widely used today are based on capacitive surfaces, which require a matrix of semiconductor-based detection elements. While they address most of the current consumer electronics market, they are limited in many respects. Among other limitations, scalability of capacitive touch screen is limited by the high number of semiconductors required. In addition, capacitive touch screens usually require costly manufacturing environment and costly material. Typically, capacitive-based solutions are inadequate for pressure determination.

Outside the consumer electronics market, other types of surfaces dedicated to pressure mapping are also used. For instance, a pressure mat can be used in conjunction with cameras to analyze behaviors of small animals (e.g., pain-related postural deficits). The pressure mat has a matrix of pressure detection cells. Each cell is connected to a management unit and delivers a pressure measurement. Among other limitations, the pressure mat is difficult to maintain in working condition (e.g., fragile surface ill-adapted to animals) and presents scalability issues (e.g., required number of cells for an appropriate density, required number of input ports for the management unit, etc.).

The present invention addresses at least some of the aforementioned problems.

SUMMARY

A first aspect of the present invention is directed to a method for determining that a pressure field is applied on a structure. The method comprises generating a plurality of acoustic waves within the structure using at least one wave generator and taking a plurality of measurements of the plurality of acoustic waves using at least one wave sensor. The method also comprises determining that a pressure field is applied to a surface of the structure by processing the plurality of measurements. The acoustic waves are scattered due, for instance, to the presence of the pressure field. The wave generator and the wave sensor may, for instance, be piezoelectric elements. The piezoelectric elements may alternate between acting as the wave generator and acting as the wave sensor.

The structure may be a thin structure made of rigid or flexible material, planar or curved and may allow the acoustic wave to be propagated therein. The acoustic waves may be propagated as guided waves.

Processing the measurements may further comprise obtaining a differential value between the measurements and comparing the differential value to a threshold.

Determining that the pressure field applied may further comprise processing the measurements using a model of acoustic wave propagation within the structure. The model may, for instance, comprise propagation speed of the plurality of acoustic waves within the structure. In addition, if the at least one wave generator and the at least one wave sensor are at known coordinates on the structure, the model may be determined by processing the measurements before storing the model in a memory. The model may be determined by performing a free-calibration while the structure is free of external pressure and/or by performing a loaded-calibration while an object of known characteristics is placed at a known location on the structure. The model may also be based on theoretical or experimental results.

The method may further comprise providing a model and determining that the pressure field is applied to the structure at a location on the surface by processing the measurements from one or more wave sensors. The method may then also further comprise determining an amplitude of the pressure field at the location on the surface by processing the measurements.

If, optionally, more than one wave sensor is provided, the method may further comprise providing a model comprising at least propagation speed of the plurality of acoustic waves within the structure and determining that the pressure field is applied to the structure at a location on the surface by processing the measurements from different wave sensors. The method may then also further comprise determining an amplitude of the pressure field at the location on the surface by processing the measurements from the different wave sensors. Optionally, correlating the measurements with the model retrieved from memory may further be performed in order to provide a mapping of the pressure field on the surface of the structure.

The method may further comprise determining that at least one object applies the pressure field on the structure. It may further be determined that the object applies the pressure field on the structure at more than one determined locations with an associated number of determined amplitudes. The object may be one or more fingers and the determined locations and determined amplitudes may allow for fingerprint determination.

The location may be determined within a predictable location tolerancing and the amplitude is determined within a predictable amplitude tolerancing.

The method may further comprise approximating, from the determination, a position of the at least one object in three dimension.

Optionally, the method may comprise obtaining a series of determinations over time. The series of determinations may be used as an input to an electronic device. It may also be determined that at least one animal applies the pressure field on the structure. The series of determinations may then be used to evaluate behaviors of the animal. The animal may be a mammal such as a rodent or a human.

A second aspect of the present invention is directed to an apparatus comprising a structure on which a pressure field is applied, a wave generator and a wave sensor. The wave generator is for generating a plurality of acoustic waves within the structure. The wave sensor is for taking a plurality of measurements of the plurality of acoustic waves. The apparatus further comprises a processing module for determining that a pressure field is applied to a surface of the structure by processing at least two of the plurality of measurements. The wave generator and the wave sensor can be piezoelectric elements. Each of the piezoelectric elements may further alternate between acting as the wave generator and acting as the wave sensor.

Processing the measurements by the processing module may further comprise obtaining a differential value between the measurements and comparing the differential value to a threshold.

Determining by the processing module that the pressure field is applied may further comprise processing the measurements using a model of acoustic wave propagation within the structure stored in a memory module of the apparatus. The model may comprise propagation speed of the plurality of acoustic waves within the structure. The model may be based on a theoretical model or experimental results.

The apparatus may also comprise a plurality of wave generators and a plurality of wave sensors. Each wave generator and each wave sensor may be at known coordinates on the structure. In such an example, the processing module may further determine the model by processing the measurements and storing the model in the memory module. The processing module further may determine the model by performing a free-calibration while the structure is free of external pressure. The processing module may further provide the model by performing a loaded-calibration while an object of known characteristics is placed at a known location on the structure.

The processing module may further provide a model and determine that the pressure field is applied to the structure at a location on the surface by processing the plurality of measurements from different wave sensors from the plurality of wave sensors.

If the apparatus comprises a plurality of wave sensors, the processing module may further provide a model comprising at least propagation speed of the plurality of acoustic waves within the structure and determine that the pressure field is applied to the structure at a location on the surface by processing the plurality of measurements from different wave sensors from the plurality of wave sensors. The model is either based on a theoretical approach or on experimental results. The processing module may further determine an amplitude of the pressure field at the location on the surface by processing the measurements from the different wave sensors. For instance, the processing module may correlate the measurements against the model retrieved from memory and provide a mapping of the pressure field on the surface of the structure from the correlated measurements. The processing module may determine that at least one object applies the pressure field on the structure. The object that applies the pressure field on the structure may be at more than one determined locations, the pressure field being of an associated number of determined amplitudes. The object may be one or more fingers and the determined locations and determined amplitudes allow for fingerprint determination. The location may be determined by the processing module within a predictable location tolerancing and the amplitude is determined within a predictable amplitude tolerancing.

The processing module may further approximate, from the determination, a position of the at least one object in three dimensions.

The processing module may further obtain a series of determinations over time. The series of determinations may be used as an input to an electronic device. The processing module may further determine that at least one animal applies the pressure field on the structure and use the series of determinations to evaluate behaviors of the animal. The animal may be a mammal such as a rodent or a human.

BRIEF DESCRIPTION OF THE DRAWINGS

Further features and exemplary advantages of the present invention will become apparent from the following detailed description, taken in conjunction with the appended drawings, in which.

DETAILED DESCRIPTION

The present invention proposes a method and an apparatus for determining that a pressure field is applied on a structure. The method and apparatus may also be used for determining the position and the strength of the pressure field applied to the structure. A plurality of acoustic waves are generated within the structure using at least one wave generator and a plurality of measurements of the plurality of acoustic waves is taken using at least one wave sensor. A pressure field applied to a surface of the structure is determined by processing at least two of the plurality of measurements. It is thought that the measurements correspond to reflections and echoes of the acoustic waves within the structure, as affected by a given pressure or pressure field. As such, the acoustic waves are scattered due, for instance, to the presence of the pressure field. The wave generator and the wave sensor may, for instance, be piezoelectric elements. The piezoelectric elements may alternate between acting as the wave generator and acting as the wave sensor. Other examples of wave generators and wave sensors include ultrasonic wedges and air-coupled ultrasonic transducers.

The structure may be a thin structure made of rigid or flexible material, planar or curved and may allow the acoustic wave to be propagated therein. The acoustic waves may be propagated as guided waves.

Processing the measurements may further comprise obtaining a differential value between the measurements and comparing the differential value to a threshold.

Determining that the pressure field is applied may further comprise processing the measurements using a model of acoustic wave propagation within the structure. The model may, for instance, comprise propagation speed of the plurality of acoustic waves within the structure. In addition, if the at least one wave generator and the at least one wave sensor are at known coordinates on the structure, the model may be determined by processing the measurements before storing the model in a memory. The model may be determined by performing a free-calibration while the structure is free of external pressure and/or by performing a loaded-calibration while an object of known characteristics is placed at a known location on the structure. The model may be based on theoretical or empirical approaches.

A model may determine that the pressure field is applied to the structure at a location on the surface by processing the measurements from different wave sensors. An amplitude of the pressure field at the location on the surface may further be determined by processing the measurements of the scattered wave due to the local pressure field. Optionally, correlating the measurements with the model retrieved from memory may further be performed in order to provide a mapping of the pressure field on the surface of the structure.

If, optionally, more than one wave sensor is provided, a model comprising at least propagation speed of the plurality of acoustic waves within the structure may be providing and it may determine that the pressure field is applied to the structure at a location on the surface by processing the measurements from different wave sensors. An amplitude of the pressure field at the location on the surface may further be determined by processing the measurements from the different wave sensors. Optionally, correlating the measurements against the model retrieved from memory may further be performed in order to provide a mapping of the pressure field on the surface of the structure.

It may further be determined that at least one object applies the pressure field on the structure. It may further be determined that the object applies the pressure field on the structure at more than one determined locations with an associated number of determined amplitudes. The object may be one or more finger and the determined locations and determined amplitudes may allow for fingerprint determination. The location may be determined within a predictable location tolerancing and the amplitude is determined within a predictable amplitude tolerancing. From the determination, a position of the at least one object in three dimension may be approximately provided.

A series of determinations may be obtained over time. The series of determinations may be used as an input to an electronic device. It may also be determined that at least one animal applies the pressure field on the structure. The series of determinations may then be used to evaluate animal behavior. The animal may be a mammal such as a rodent or a human.

The present invention relates to a method and an apparatus that can be used for determining the spatiotemporal distribution of at least one pressure level applied on a surface of a structure. As will be detailed herein, some structures allow for acoustic waves to be propagated therein. In some structures, the acoustic waves will be propagated as guided waves. For instance, thin structures usually allow for ultrasonic acoustic waves to be propagated as guided waves. Reflection and dispersion of the guided waves can then be modeled within the structure. It has been determined that a pressure field applied to the modeled structure at one or more specific locations predictably affect the reflection and dispersion of the acoustic waves. As such, based on the model, it is possible to determine applied pressure and amplitude of at least one applied pressure. Curved or irregular structures (e.g., those structures that can be modeled) would also be suitable in the context of the present invention. Various parameters are known to affect the precision of the determination of location and amplitude. Some parameters can be set in order to obtain an expected precision (e.g., depending on the expected use of the determination).

Figure 1:
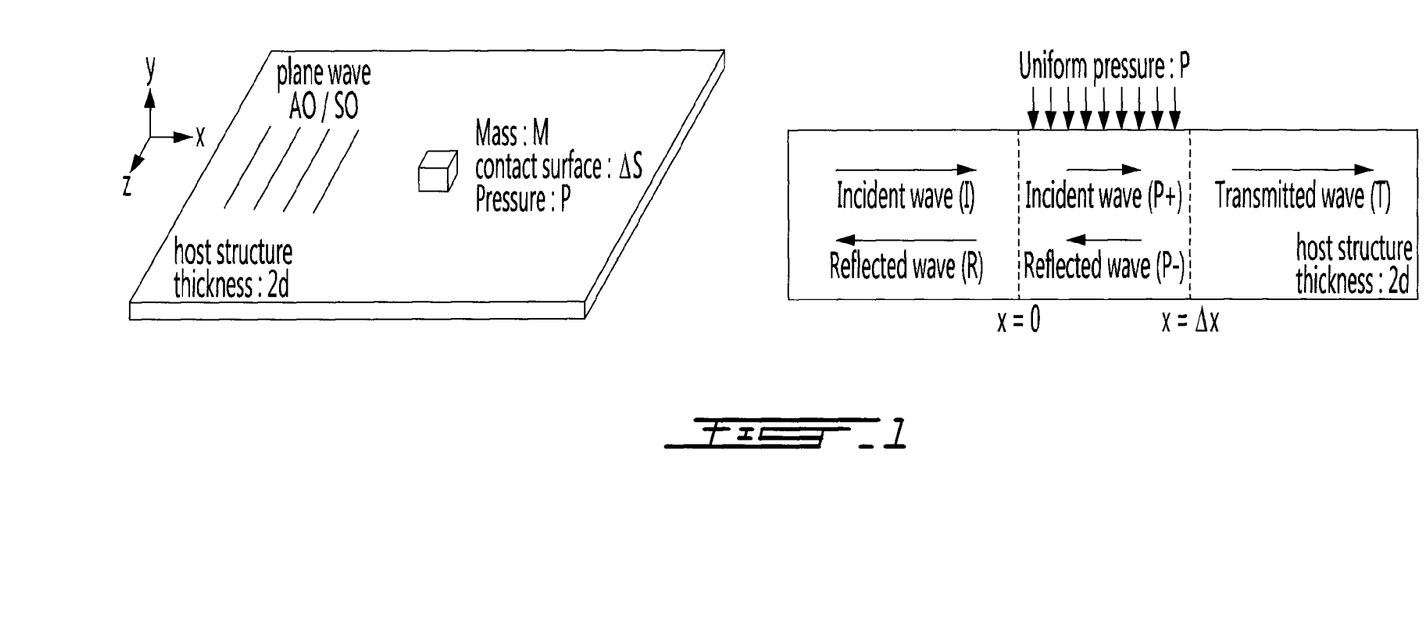
FIG. 1 is a schematic diagram representing exemplary interactions of acoustic waves in the presence of a local pressure field, in accordance with the teachings of the present invention.

The present invention is based on the interaction of acoustic waves in the presence of a local pressure field. Reference is now made to the drawings in which FIG. 1 shows a schematic diagram representing exemplary interactions of acoustic waves (I) in the presence of a local pressure field (P), in accordance with the teachings of the present invention. The current state of the research performed suggests that the local contact of an object on a structure is responsible for three different effects.

Firstly, it appears that the object creates a reaction force into the host structure, such that a local deformation is observed. However, the local change of thickness is not seen as important (few microns), even on a very flexible structure. In this case, the current research suggests that the propagation of waves is not impaired by this phenomenon and no local reflection is induced.

Secondly, another effect of local added object is that part of the energy appears to be transmitted into the object, responsible for a loss of transmitted energy. This effect can be observed when a perfect contact is ensured between the host structure and the added object and when the acoustic impedances of both structures are similar. However, for sensitive surfaces, such as touch-screens or pressure mapping solutions, the sensed object is expected to be a tissue with associated low acoustic impedance compared to metallic or polymer structures. Thus, in the context of the present invention, it appears that this effect can be neglected when considering the interaction of an acoustic wave with a local added mass.

Thirdly, an added mass M applied at the surface of a thin structure appears to create a local change of surface stress, such that the propagation of acoustic waves, and especially guided waves (for instance A0 and S0 modes), is locally modified. The added mass M applied over a surface S can be described as a local change of boundary stresses (equations are not necessary since it is an approximation).

This local change of boundary condition at the contact appears to induce a change of propagation characteristics. Indeed, in the absence of added mass, the dispersion relation is obtained by considering the traction free boundary conditions at the upper and lower surfaces of the plate while in the presence of added mass M distributed over a surface S, the resulting pressure P is responsible for a local change of the stress field at the upper boundary, while the other boundary remains free of stress, leading to a new dispersion relation (local change of phase and group velocities at the contact) as presented in FIG. 2.

Figure 2A:
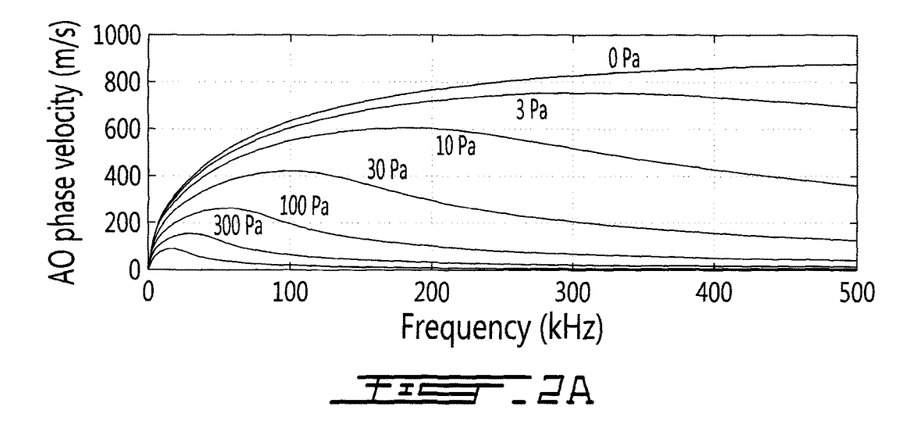
FIGS. 2A and 2B, referred to together as FIG. 2, present graphs illustrating an evolution of the phase velocity for A0 mode (2A) and S0 mode (2B) in a surface under a pressure, in accordance with the teachings of the present invention.
Figure 2B:
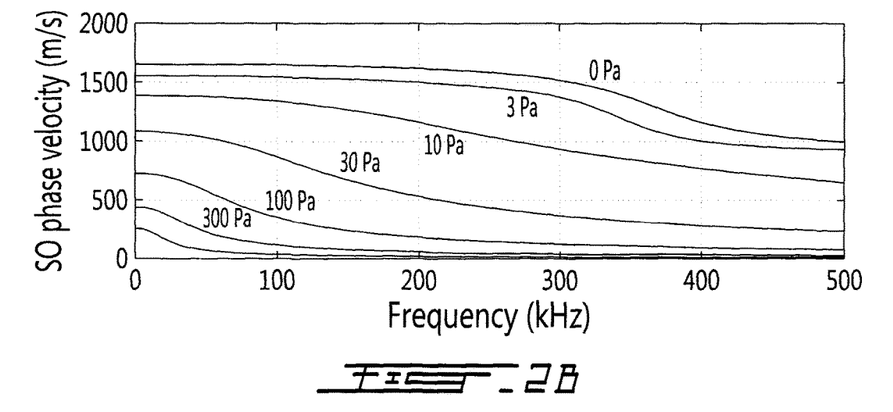

In that case, the mode shapes associated with propagating modes (antisymmetric A0 and symmetric S0) are strongly modified and surface waves are mostly observed in the contact region. This local change of propagating modes induces reflection of acoustic waves in the medium that may be estimated theoretically and is related to:

Material properties (Young's modulus, density and Poisson's ratio),
Thickness of the host structure,
Frequency of incident field,
Mode of the incident wave (symmetric, antisymmetric, Shear-Horizontal, Surface wave),
Surface of contact of the mass,
Added pressure.

Figure 3:
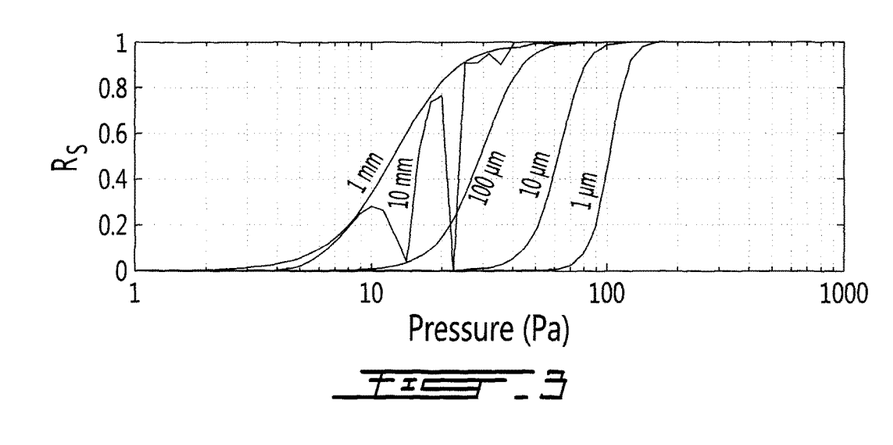
FIG. 3 is a graph illustrating an evolution of a reflection coefficients in an exemplary 0.25 mm thick polycarbonate structure associated with S0 mode at 100 kHz with respect to the local pressure for different lengths of application $\Delta x$, in accordance with the teachings of the present invention.

As an example, FIG. 3 represents the evolution of the reflection coefficient associated with S0 mode at 100 kHz with respect to the added pressure for a 0.25 mm thick polycarbonate structure for various pressure application lengths. In FIG. 3, it appears that no reflections are observed below 3 Pa no matter the contact length. Moreover, above 100 Pa, the reflection of S0 mode is total (reflection coefficient of 1), defining a range of detectable pressure levels. Those minimal and maximal pressure values define the pressure sensitivity range, depending on the desired application and are related to the material properties and thickness only.

Some parameters of interest that have been determined during prototype design will now be discussed. The interaction of a pressure wave with a local pressure has been discussed hereinabove. For detection and evaluation of pressure field, the reflection coefficient at the contact may be mapped using an imaging algorithm (e.g., EUSR, Excitelet, etc). Sensitivity to an applied pressure or pressure field will be determined by parameters of the host structure and propagation characteristics therewithin. More specifically, depending on the application, requirements can be defined:

Pressure sensitivity: A given application likely provides a requirement of sensitivity within a given range of pressure. Thus, minimal and maximal pressures are to be defined. It appears that those parameters are related to the material thickness and properties (Young's modulus, density and Poisson's ratio). In the case of touch screen applications, for instance, pressure levels from 10 to 10000 Pa have been identified, such that thin structures (below 1 mm) with Young's modulus above 5 GPa can be employed.

Imaging precision: According to the research conducted, the mode and frequency of an acoustic wave will determine if imaging of the pressure field is possible. Indeed, the frequency and mode selection determines the wavelength $\lambda$ of the generated wave. The imaging precision is related to this wavelength and imaging spot surfaces are of the order of $\lambda^2$. For touch screen application, for instance, a wavelength of approximately 5 mm could be used. The choice of mode, frequency and piezoceramic size are derived from this value after selecting the material properties. Moreover, the precision of imaging contour is related to the number of wave generators and sensors used in the application. The precision of imaging contour may also be related to the number of units and the quality of the signal processing algorithm.

Signal to noise ratio (SNR): For proper imaging for real-time application, reflected signals must be measured with high SNR. The amplitude of the reflected signal is affected by the actuator energy sent (e.g., the wave generator energy) into the host structure, the propagation distance between emitter, reflector and sensor, the sensor sensitivity and wave attenuation which is related to mode, frequency and material damping. For large applications (above 0.5 m), it has been determined that A0 mode on metallic structures can be employed due to its low attenuation coefficient. For smaller applications, it appears that polymers with low damping coefficients should be employed. Piezoceramic characteristics (material, size and thickness) influence the actuator and sensor characteristics. Commonly, circular piezoceramics of 2 mm to 10 mm diameter and 0.5 mm thickness are used.

Real-time application: Depending on the refresh rate of the application (number NI of images per second), the acquisition parameters can be derived. Indeed, the averaging A and acquisition time T can be determined using the relation: $NI=1/A*T$. The number N of transducer units, the sampling rate Fs and size of grid for imaging are determined by the limitations of the processing unit. For portable application (FPGA integration, for instance), 8 units processed at 10 MHz can be used for imaging over a grid of 100×100 pixels.

Figure 4:
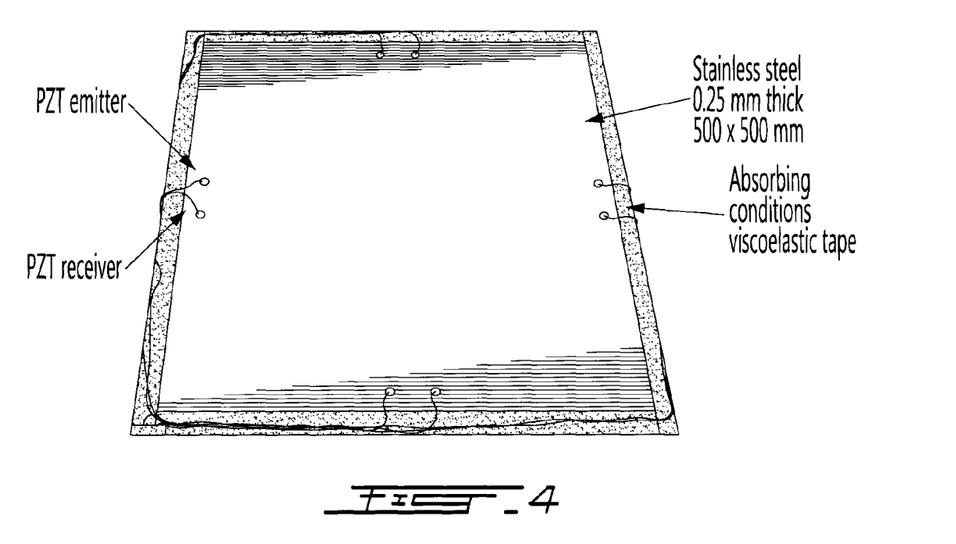
FIG. 4 is a visual representation of an exemplary prototype used for development in accordance with the teachings of the present invention.

In the course of the research work performed, an exemplary prototype has been developed for determination of pressure field for touch screen application over a large surface. The sensitive part is composed of the 0.25 mm thick stainless steel plate. The plate dimensions are 500×500 mm and it is instrumented with 8 piezoceramics (4 actuators and 4 sensors) of 10 mm diameter and 0.25 mm thickness located at the periphery. In the context of the present prototype, an absorbing layer (viscoelastic tape) is added at the edges in order to prevent reflections from the boundaries. FIG. 4 is a visual representation of an exemplary prototype used for development in accordance with the teachings of the present invention.

Figure 5:
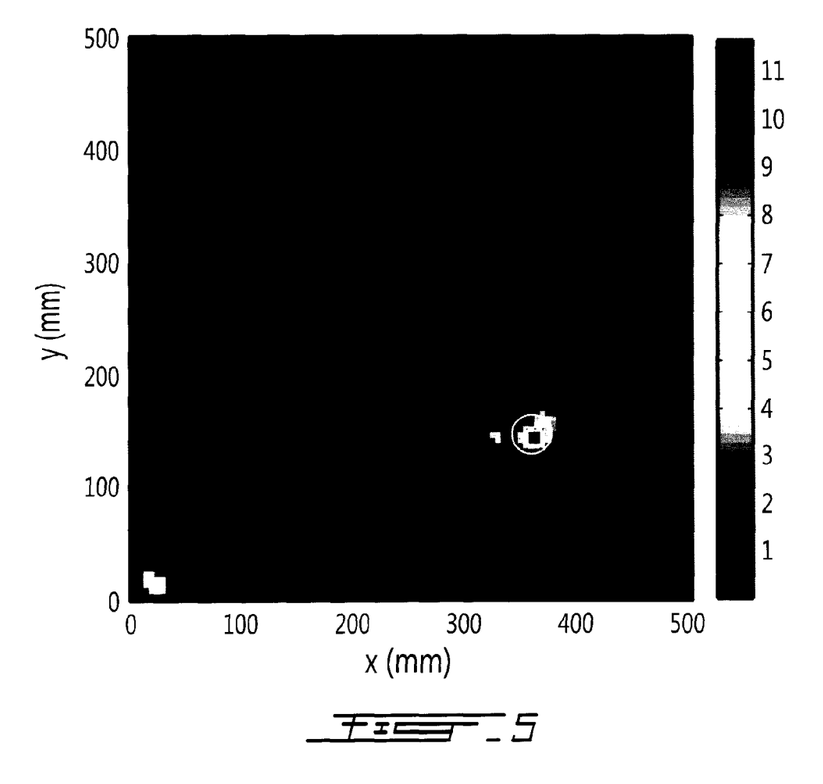
FIG. 5 is an exemplary imaging result obtained from the exemplary prototype using a 1 kg mass over a 6 mm×6 mm area in accordance with the teachings of the present invention.

The signal generation, acquisition and processing can be performed by a dedicated platform (NI PXI 7962) and analysis is performed using Matlab application. For embedded solution, implementation on a Field Programmable Gate Arrays (FPGA) card can be envisaged. FIG. 5 shows an exemplary imaging result obtained from the exemplary prototype of FIG. 4 using a 1 kg mass over a 6 mm×6 mm area.

An exemplary flow chart will now be described with particular reference to the exemplary prototype of FIG. 4. Each unit (actuator/sensor/processing) acts independently of the other. However for imaging of the whole structure, the measured signals from each unit are used in order to determine the location and intensity of the receiver. Thus, the steps of the exemplary flowchart are performed for each time step between two consecutive pressure mapping results.

1. Signal generation
   N cycles burst (typically N=5.5)
   Central frequency (typically f=300 kHz)
2. Signal acquisition
   Averaging (typically 10 to 100)
   Recording length (typically 1 ms)
   Sampling frequency (typically 10 MHz)
3. Signal processing
   denoising (band pass filtering)
   reference subtraction
4. Imaging
   Grid of imaging points (typically 100×100)
   Processing algorithm (EUSR, Excitelet)
   Number of units (typically 4 to 8)
5. Feature extraction
   Maximum detection
   Pressure determination
   Tracking As mentioned previously, in the context of the present invention, it has been found that generating the waves in the structure was best achieved by using a piezoelectric element, acting as a generator, at the periphery of the structure of interest. A plurality of piezoelectric elements, acting as piezoelectric sensors, then measure the response of the structure to the waves. It has also been determined that by using a plurality of piezoelectric elements, they could be used, in turn, as the wave generator and piezoelectric sensors. For instance, the piezoelectric elements (or piezoelectric ceramics) may be permanently fixed to the structure (e.g., glued or eventually built in). The response of the structure to the waves is collected as a plurality of signals. As mentioned above, it is thought that the signals correspond to reflections and echoes of the waves within the structure, as affected by a given pressure or pressure field. However, an important exemplary advantage with regard to the industrial applicability of the solution is that the plurality of signals collected allow to predictably represent location and amplitude of at least one pressure applied to the structure.

Based on the model derived from the structure, a determination can then be made on an eventual pressure applied to the surface. For example, it has been found that using an imaging tool such as Embedded Ultrasonic Structural Radar (EUSR) and/or Excitelet (as mentioned in the referenced document), allows for determining a signature of the collected signals and to plot a two-dimensional map of the structure.

Figure 6:
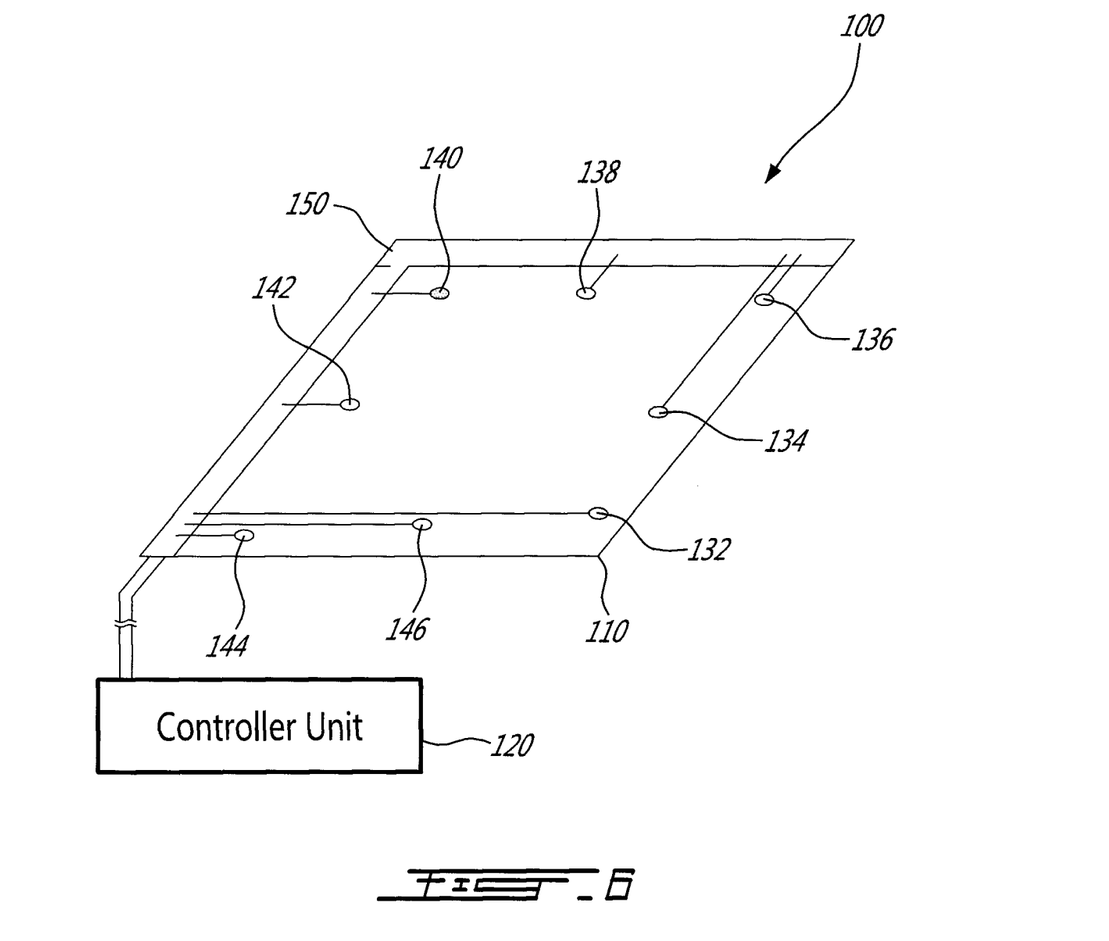
FIG. 6 is a perspective view of an exemplary apparatus in accordance with the teachings of the present invention.

FIG. 6 shows a perspective view of an exemplary apparatus 100 in accordance with the teachings of the present invention. A structure 110 is provided with a plurality of transducers 132-146 thereon. The transducer 140 is illustrated in a different shade to illustrate that it functions as an ultrasonic wave generator while the other transducers 132-138, 142-146 function as wave sensors. The transducers are shown connected to an exemplary data bus 150, which connects the transducers to a controller unit 120. Skilled person will understand that only one generator is shown, but that a plurality of generators may be used in order to increase precision to a desired level. Still in order to increase precision, the transducers 132-146 may exchange their role as generator and sensors.

It is noticed that, under the effect of a pressure applied by an object (not shown) on the structure 110, the wave pattern changes and can be measured by the transducers 132-146 then acting as wave sensors. In the context of the example of FIG. 6, the measurements can be passed on to the controller unit 120 where it can be processed to identify a position in the plane and to determine pressure data with respect to the measurements. For additional precision, processing may be improved with the use of three or more sensors.

Mapping tools such Embedded Ultrasonic Structural Radar (EUSR) and/or Excitelet may then be used to establish a spatial mapping of locations and amplitudes of the applied pressure. Interpretation of the results obtained by these imaging algorithms is enhanced by knowledge of the mechanical properties of the structure 110. Calibration may be required in order to precisely identify the properties and material of the structure 110 may need to be changed to achieve desired results.

Figure 7:
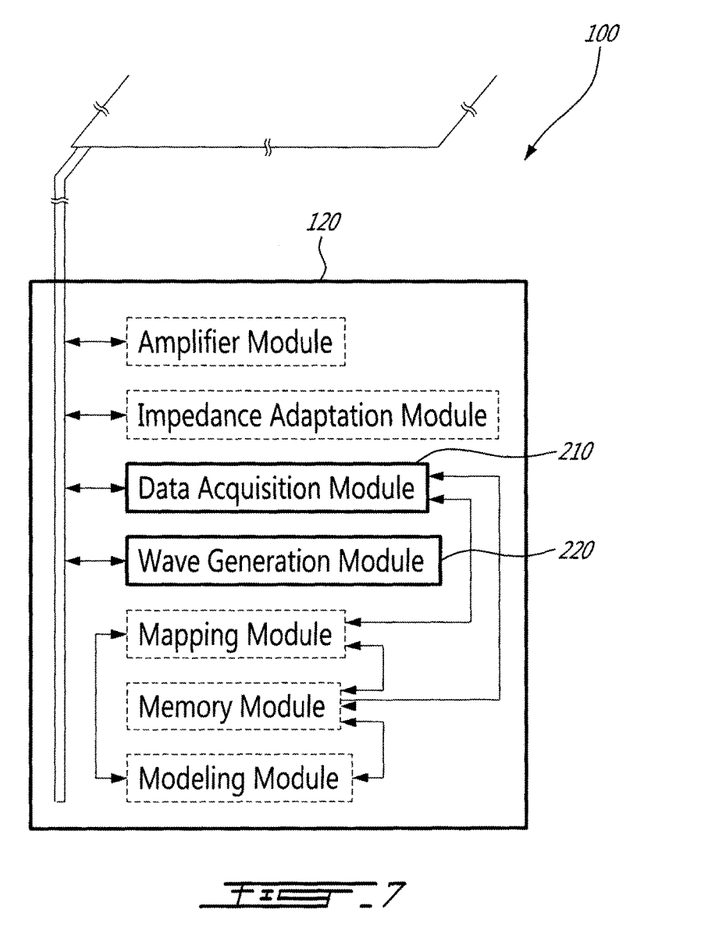
FIG. 7 is a modular representation of an exemplary controller unit in accordance with the teachings of the present invention.

FIG. 7 shows a modular representation of the exemplary controller unit 120 in accordance with the teachings of the present invention. The controller unit 120 comprises a data acquisition module 210 for obtaining the measurements from the transducers 132-138, 140-146 and a wave generation module for controlling the transducer 140. As mentioned above, the wave generation module 220 may further use more than one of the transducers 132-146 as wave sensors and/or more than one of the transducers 132-146 as wave generator(s). The wave generation module 220 may further control the transducers 132-146 so that they exchange their role as generator and sensors (e.g. please provide range of frequency).

Thus, by applying an electrical signal pulse having a center frequency (e.g., typically in the order of several hundred kilohertz as a burst), it becomes possible to generate a wave propagating in a guided manner, within the structure, over the time and space. Generated waves are attenuated differently in different materials. Viscoelastic material (e.g. elastomers) tend to attenuate waves rapidly while, conversely, large propagation distances can be reached in the case of low viscoelastic materials (e.g. Corning's Gorilla Glass 2, metals and amorphous polymers).

The location of sources of reflection (e.g., position of object on the structure 110) may be obtained by processing of measurements. The transducers 132-146 (e.g., piezoelectric ceramics) may be distributed over the structure 110 or its periphery (sparse array) or condensed in order to achieve an antenna (compact array).

In order to derive a map of the pressure amplitude on the structure 110, an imaging tool can be used (such Embedded Ultrasonic Structural Radar (EUSR) or Excitelet). EUSR is based on the estimate of the position of a reflector using time data spread (Time-of-Flight), which ignores the dispersive nature of waves propagating. The result is a rapid but imprecise determination. Excitelet is based on the correlation of measured reflections with synthetic signals from the theoretical propagation or experimental measurements (e.g. model) of the waves. The Excitelet can detect defects in thin structures and it appears advantageous to use this approach in this case, at least for applications requiring higher precision. A mix of both techniques may also be used (e.g., depending on an application running on an electronic product which has the structure 110 as an input device). For instance, in tests performed in a research context with two identical objects, EUSR shows the extent of pressure areas but the relative intensity of each differs while Excitelet shows the two pressure zones with the same intensity (with less than 10% error).

In the context of the research performed, it appears that the size of the area to be inspected is limited by the spread of waves. Indeed, any material has a coefficient representing the rate viscoelastic damping mechanical waves therein. Also, the material and the frequencies of waves generated should be chosen carefully in view of the desired application to ensure that the echo can be spread without limitation, other than the deformation, to the sensors. The expected sizes for this type of application can range from a few centimeters (e.g., graphic palettes) to more than one meter (e.g., medical and oversized touch screen).

If robustness to external stress is a criteria, the material should then have a strong resistance to external shocks. This is characterized by a large yield (of the order of several hundreds of MPa).

To obtain better imaging results, is appears that waves generated are to be as little dispersive as possible and a limited number of modes propagation should be respected. These parameters can be adjusted by controlling the size of piezoelectric ceramics, their positioning, the frequencies of electrical signals sent and the characteristics of the propagation medium (thickness and materials).

The quality of the results obtained by the imaging algorithms is improved by knowledge of mechanical properties of the propagation. The accuracy of the pressure mapping depends on the imaging algorithm implemented and the desired response time. At the present stage of development, the use of Field Programmable Gate Arrays (FPGA) have allowed using the Excitelet algorithm with a 100×100 grid and achieve 25 frames per second.

More specifically, in the example of the prototype achieving real-time performance (e.g., 25 frames per second), processing is performed by a high-speed FPGA in coordination with LabVIEW. The imaging algorithm (e.g., EUSR, Excitelet, etc.) is implemented on the dedicated FPGA, which then performs data acquisition operations and image processing. In the present example, an electronic signal conditioning has also been developed to adapt the impedance of the sensor and pre-amplify the signals. It is expected that dedicated solutions will keep improving on those results and provide diverse real-time ranges of sensitivity and size.

Figure 8:
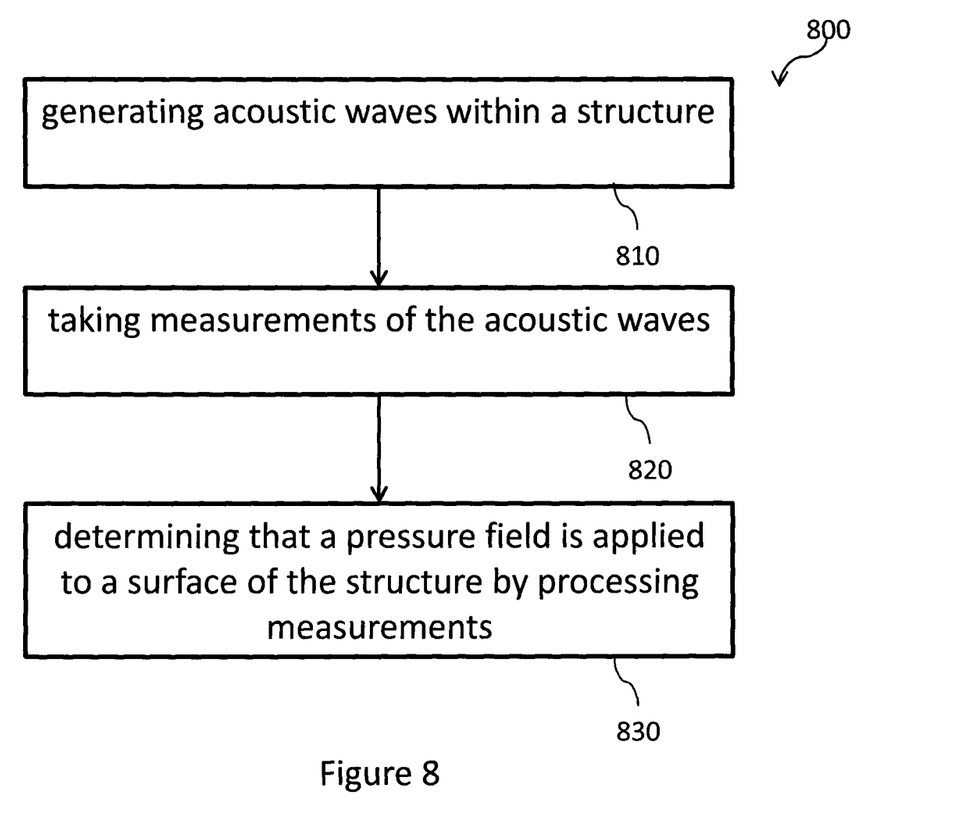
FIG. 8 is a flow chart of an exemplary method for determining that a pressure field is applied on a structure in accordance with the teachings of the present invention.

FIG. 8 shows a flow chart of an exemplary method for determining that a pressure field is applied on a structure in accordance with the teachings of the present invention. The method comprises generating a plurality of acoustic waves within the structure using at least one wave generator 810 and taking a plurality of measurements of the plurality of acoustic waves using at least one wave sensor 820. The method also comprises determining that a pressure field is applied to a surface of the structure by processing the plurality of measurements 830. The acoustic waves are scattered due, for instance, to the presence of the pressure field. The wave generator and the wave sensor may, for instance, be piezoelectric elements. The piezoelectric elements may alternate between acting as the wave generator and acting as the wave sensor.

To demonstrate functional and economical viability of the present invention, new prototypes that are more compact are under research. The treatment of signals is of specific interest. A larger number of sensors are expected in the new prototypes. A structure of 1 m×1 m is under development for specific application to the medical field. Requirements in terms of detectability and measurement accuracy will also be determined with respect to data required by the partners in the medical field.

In the context of the present invention, a processor module may represent a single processor with one or more processor cores or an array of processors, each comprising one or more processor cores. A memory module may comprise various types of memory (different standardized or kinds of Random Access Memory (RAM) modules, memory cards, Read-Only Memory (ROM) modules, programmable ROM, etc.). A storage devices module may represent one or more logical or physical as well as local or remote hard disk drive (HDD) (or an array thereof). The storage devices module may further represent a local or remote database made accessible to a network node by a standardized or proprietary interface. A network interface module represents at least one physical interface that can be used to communicate with other network nodes. For the sake of simplicity, the following example related to the network node will refer to a repository to represent the various means that can be used to store records. The network interface module may be made visible to the other modules of the network node through one or more logical interfaces. The actual stacks of protocols used by the physical network interface(s) and/or logical network interface(s) of the network interface module do not affect the teachings of the present invention. The variants of processor module, memory module, network interface module and storage devices module usable in the context of the present invention will be readily apparent to persons skilled in the art. Likewise, even though explicit mentions of the memory module and/or the processor module are not made throughout the description of the present examples, persons skilled in the art will readily recognize that such modules are used in conjunction with other modules of the network node to perform routine as well as innovative steps related to the present invention.

A method is generally conceived to be a self-consistent sequence of steps leading to a desired result. These steps require physical manipulations of physical quantities. Usually, though not necessarily, these quantities take the form of electrical or magnetic signals capable of being stored, transferred, combined, compared, and otherwise manipulated. It is convenient at times, principally for reasons of common usage, to refer to these signals as bits, values, parameters, items, elements, objects, symbols, characters, terms, numbers, or the like. It should be noted, however, that all of these terms and similar terms are to be associated with the appropriate physical quantities and are merely convenient labels applied to these quantities. The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses.

The invention claimed is:

1. A method for determining that a pressure field is applied on a structure, the method comprising:
   generating a plurality of acoustic waves within the structure using at least one wave generator;
   taking a plurality of measurements of the plurality of acoustic waves using at least one wave sensor;
   determining a model, specific to the structure, of acoustic wave propagation within the structure from the plurality of measurements by performing:
      a free-calibration while the structure is free of external pressure; and
      a loaded-calibration while an object of known characteristics is placed at a known location on the structure;
   subsequently to the determination of the model, determining that a pressure field is applied to a surface of the structure by processing at least two of the plurality of measurements;
   correlating the at least two measurements with the model of acoustic wave propagation within the structure; and
   providing a two-dimensional mapping of the pressure field on the surface of the structure from the correlated measurements.

2. The method of claim 1, wherein the wave generator and the wave sensor are piezoelectric elements.

3. The method of claim 2, wherein each of the piezoelectric elements alternate between acting as the wave generator and acting as the wave sensor.

4. The method of claim 1, wherein the structure is a thin structure made of rigid or flexible material, wherein the structure is planar or curved and allows the acoustic wave to be propagated therein as guided waves.

5. The method of claim 1, wherein processing the measurements further comprises obtaining a differential value between the measurements and comparing the differential value to a threshold.

6. The method of claim 1, wherein the model comprises propagation speed of the plurality of acoustic waves within the structure.

7. The method of claim 1, wherein a plurality of wave sensors are provided and wherein
determining that the pressure field is applied to the structure at a location on the surface and correlating the at least two measurements is performed by processing the plurality of measurements from different wave sensors from the plurality of wave sensors.

8. The method of claim 7, further comprising determining an amplitude of the pressure field at the location on the surface by processing the measurements from the different wave sensors.

9. The method of claim 7, further comprising determining that at least one object applies the pressure field on the structure.

10. The method of claim 9, further comprising determining that the at least one object applies the pressure field on the structure at more than one determined locations, the pressure field being of an associated number of determined amplitudes.

11. The method of claim 10, wherein the at least one object is one or more finger and the determined locations and determined amplitudes allow for fingerprint determination.

12. The method of claim 7, wherein the location is determined within a predictable location tolerancing and the amplitude is determined within a predictable amplitude tolerancing.

13. The method of claim 9, further comprising approximating, from the determination, a position of the at least one object in three dimensions.

14. The method of claim 1 further comprising obtaining a series of determinations over time.

15. The method of claim 14, further comprising using the series of determinations as an input to an electronic device.

16. The method of claim 14, further comprising:
determining that at least one animal applies the pressure field on the structure; and
using the series of determinations to evaluate behavior of the animal.

17. The method of claim 16, wherein the animal is a mammal such as a rat or a human.

18. An apparatus comprising:
a structure on which a pressure field is selectively applied:
a wave generator for generating a plurality of acoustic waves within the structure;
a wave sensor for taking a plurality of measurements of the plurality of acoustic waves;
a memory module that stores a model specific to the structure, of acoustic wave propagation within the structure:
a processing module for:
while the pressure field is not applied to the structure, determining the model of acoustic wave propagation within the structure from the plurality of measurements by performing:
a free-calibration while the structure is free of external pressure; and
a loaded-calibration while an object of known characteristics is placed at a known location on the structure;
subsequently to the determination of the model, determining that the pressure field is applied to a surface of the structure by processing at least two of the plurality of measurements;
correlating the at least two measurements with the model of acoustic wave propagation within the structure; and
providing a two-dimensional mapping of the pressure field on the surface of the structure from the correlated measurements.

19. The apparatus of claim 18, wherein the wave generator and the wave sensor are piezoelectric elements.

20. The apparatus of claim 19, wherein each of the piezoelectric elements alternate between acting as the wave generator and acting as the wave sensor.

21. The apparatus of claim 18, wherein the structure is a thin structure made of rigid or flexible material, wherein the structure is planar or curved and allows the acoustic wave to be propagated therein as guided waves.

22. The apparatus of claim 18, wherein processing the measurements by the processing module further comprises obtaining a differential value between the measurements and comparing the differential value to a threshold.

23. The apparatus of claim 18, wherein the model comprises propagation speed of the plurality of acoustic waves within the structure.

24. The apparatus of claim 18, wherein the model is based on a theoretical model or experimental results.

25. The apparatus of claim 18 further comprising a plurality of wave generators comprising the wave generator and a plurality of wave sensors comprising the wave sensor, wherein each wave generator and each wave sensor is at known coordinates on the structure.

26. The apparatus of claim 18, wherein the apparatus further comprises a plurality of wave sensors comprising the wave sensor,
and wherein determining that the pressure field is applied to the structure at a location on the surface and correlating the at least two measurements is performed by processing the plurality of measurements from different wave sensors from the plurality of wave sensors.

27. The apparatus of claim 26, wherein the processing module further determines an amplitude of the pressure field at the location on the surface by processing the measurements from the different wave sensors.

28. The apparatus of claim 26, wherein the processing module further determines that at least one object applies the pressure field on the structure.

29. The apparatus of claim 28, wherein the processing module further determines that the at least one object applies the pressure field on the structure at more than one determined locations, the pressure field being of an associated number of determined amplitudes.

30. The apparatus of claim 29, wherein the at least one object is one or more finger and the determined locations and determined amplitudes allow for fingerprint determination.

31. The apparatus of claim 26, wherein the location is determined by the processing module within a predictable location tolerancing and the amplitude is determined within a predictable amplitude tolerancing.

32. The apparatus of claim 18, wherein the processing module further approximates, from the determination, a position of the at least one object in three dimensions.

33. The apparatus of claim 18, wherein the processing module further obtains a series of determinations over time.

34. The apparatus of claim 33, wherein the series of determinations is used as an input to an electronic device.

35. The apparatus of claim 33, wherein the processing module further:
determines that at least one animal applies the pressure field on the structure; and
uses the series of determinations to evaluate behavior of the animal.

36. The apparatus of claim 35, wherein the animal is a mammal such as a rodent or a human.

* * * * *